(12) United States Patent  
Abe et al.

(10) Patent No.: US 10,173,071 B2
(45) Date of Patent: Jan. 8, 2019

(54) MEDICAL SUCCESSIVE MAGNETIC PULSE GENERATION DEVICE

(71) Applicants: IFG Corporation, Sendai-shi, Miyagi (JP); Tohoku University, Sendai-shi, Miyagi (JP); Japan Basic Material Co., Ltd., Sendai-shi, Miyagi (JP)

(72) Inventors: Toshihiko Abe, Sendai (JP); Hitoshi Mori, Sendai (JP); Kenji Yashima, Sendai (JP); Kazumi Mori, Sendai (JP); Toshiyuki Takagi, Sendai (JP); Shinichi Izumi, Sendai (JP); Hiroyasu Kanetaka, Sendai (JP); Ryoichi Nagatomi, Sendai (JP)

(73) Assignee: IFG CORPORATION, Miyagi (JP)

( * ) Notice: Subject to any disclaimer, the term of this patent is extended or adjusted under 35 U.S.C. 154(b) by 406 days.

(21) Appl. No.: 14/906,444

(22) PCT Filed: Sep. 1, 2014

(86) PCT No.: PCT/JP2014/004470
§ 371 (c)(1),
(2) Date: Jan. 20, 2016

(87) PCT Pub. No.: WO2015/083305
PCT Pub. Date: Jun. 11, 2015

(65) Prior Publication Data
US 2016/0151637 A1 Jun. 2, 2016

(30) Foreign Application Priority Data
Dec. 3, 2013 (JP) .................. 2013-250624

(51) Int. Cl.
*A61N 2/02* (2006.01)
*A61N 2/00* (2006.01)

(52) U.S. Cl.
CPC ............... *A61N 2/02* (2013.01); *A61N 2/006* (2013.01)

(58) Field of Classification Search
CPC .................................. A61N 2/02; A61N 2/006
See application file for complete search history.

(56) References Cited

U.S. PATENT DOCUMENTS 5,738,625 A * 4/1998 Gluck .................... A61N 2/006
128/897
2009/0105522 A1 4/2009 Yi et al.
2010/0152522 A1* 6/2010 Roth ...................... A61N 2/006
600/13

FOREIGN PATENT DOCUMENTS

GB 2298370 A 9/1996
JP 57022770 A 2/1982
(Continued)

OTHER PUBLICATIONS

Office Action dated Jun. 12, 2017 from corresponding European Patent Application No. 14868312.1; Total of 8 pages.
(Continued)

*Primary Examiner* — Kaylee R Wilson
(74) *Attorney, Agent, or Firm* — Lucas & Mercanti, LLP

(57) ABSTRACT

A smaller-sized, more lightweight, and power-saving successive magnetic pulse device is provided. A discharging circuit section K is configured by connecting, in series in a loop, a magnetic therapy pulse coil 6 configured to generate an eddy current in a target part 3, a charging/discharging capacitor 4, and a switching semiconductor element 7 configured to supply a discharge current from the charging/discharging capacitor 4 to the pulse coil 6. A step-up transformer 1 includes a primary-side coil 1a connected to an AC power supply 2 and a secondary-side coil 1b connected to input terminals 5a of a full-wave rectifying circuit 5. A control unit 8 is connected to a switching semiconductor (Continued)

element 7 and controls conduction timing of the switching semiconductor element 7. The full-wave rectifying circuit 5 has output terminals 5b connected to both terminals P1 and P2 of the charging/discharging capacitor 4, respectively. An inductor 9 is connected between the output terminal 5b of the full-wave rectifying circuit 5 and the terminal P1 of the charging/discharging capacitor 4.

4 Claims, 8 Drawing Sheets

(56) References Cited

FOREIGN PATENT DOCUMENTS

| JP | S59197262 A | 11/1984 |
|----|----|----|
| JP | S60176320 A | 9/1985 |
| JP | H02243169 A | 9/1990 |
| JP | 09276418 A | 10/1997 |
| JP | H11511661 A | 10/1999 |
| JP | 2003009548 A | 1/2003 |
| JP | 2004255104 A | 9/2004 |
| JP | 2008522572 A | 6/2008 |
| JP | 2010200446 A | 9/2010 |
| WO | 2004087255 A1 | 10/2004 |
| WO | 2011083097 A1 | 7/2011 |

OTHER PUBLICATIONS

Machine translation of WO2011/083097.
International Search Report dated Oct. 7, 2014 for Application No. PCT/JP2014/004470 and English translation.
Supplemental Extended European Search Report dated Jul. 28, 2016 for corresponding European Application; Application No./Patent No. 14868312.1-1659 / 3009167 PCT/JP2014004470; Total of 6 pages.
Office Action dated Sep. 30, 2016 from corresponding Chinese Application; Patent Application No. 20140038847.7; Total of 9 pages.

* cited by examiner

MEDICAL SUCCESSIVE MAGNETIC PULSE GENERATION DEVICE

CROSS REFERENCE TO RELATED APPLICATION

This Application is a 371 of PCT/JP2014/004470 filed on Sep. 1, 2014 which, in turn, claimed the priority of Japanese Patent Application No. JP2013-250624 filed on Dec. 3, 2013, both applications are incorporated herein by reference.

TECHNICAL FIELD

The present invention relates to a medical successive magnetic pulse generation device for causing sustained great contraction in muscles by stimulating peripheral nerves with successive magnetic pulses.

BACKGROUND ART

A pulse current is used in wide industrial fields, and many products including industrial high-voltage pulse devices, such as an electric dust collector, a plasma generator, and a laser, and medical low-frequency therapeutic devices for moving muscles with a weak pulse current, have been put into practical use. Many pulse currents for industrial equipment are characterized by a high voltage (3 to 10 kV), a low current (several milliamperes to several amperes), a high frequency (30 to 100 kHz), and a narrow pulse width (1 to 10 μs). The reason for this is that as the voltage is higher and the pulse width is narrower, higher energy can be generated momentarily.

Regarding such a pulse power supply for the purpose of generating a sharp high-voltage pulse, many patent applications have been filed. Patent Literature 1 discloses a "pulse compression technique" to cascade-connect resonant circuits, each including a capacitor and a coil, for the purpose of generating a high-voltage ultrashort pulse. Each coil used in a pulse compression circuit is a saturable reactor in which a core becomes saturated when a current at a certain level or higher flows therethrough, and the coil serves both for LC resonance and as a switching element in which a coil current suddenly increases due to magnetic saturation.

Patent Literature 2 discloses a method for stabilizing a pulse voltage. For this purpose, the method is characterized in that a charging/discharging capacitor and a plurality of inductors (coils) are connected in series and each inductor forms an LC resonant circuit including an individual capacitor, a power supply, and a switch, and timings of these multiple resonant circuits are shifted from each other, thereby stabilizing a pulse voltage. Each coil in this invention is not a saturable reactor, a resonance frequency is high, and an air-core coil is used. Thus, there is no problem of saturation of a core.

As pulse current-using equipment used in the medical field, there is a low-frequency therapeutic device. According to Patent Literature 3, muscle contraction can be caused by stimulating peripheral nerves with a pulse current having a pulse width 50 μs to 1 ms with a voltage of 100 V or lower (about several milliamperes) through an electrode attached to the skin. The low-frequency therapeutic device can cause muscle contraction with low electric power, and thus the size of the device can be very small. However, it takes time and effort to attach the electrode to the skin, and in the case of causing great muscle contraction, there is a problem that great pain is involved, since electric stimulation is an electric shock. If the electrode is buried under the skin, the problem of pain can be avoided, but there is a problem that purulence is likely to occur from a portion where an electrode wire contacts the skin.

As pulse current application medical equipment different from a low-frequency therapeutic device, there is a magnetic stimulation device. This device employs a method of stimulating nerves with an induced current generated by magnetic pulses, and has an advantage that it is unnecessary to attach an electrode to the skin. In the magnetic stimulation, a pulse current having a voltage of about 1400 V, a current of about 2000 A, and a pulse width of about 0.2 milliseconds is caused to momentarily flow through a magnetic stimulation coil to generate a strong magnetic field, and an induced current is generated in the living body by the magnetic field, thereby stimulating nerves. The electric energy of one pulse in this case is generally about 100 joules. Meanwhile, in the case of the industrial pulse power supply described above, the voltage is about 10 kV, the current is about 100 mA, the pulse width is about 1 μs, and the electric energy of one pulse is about one several hundredth of joules and is much lower than that of the magnetic stimulation pulse.

Patent Literature 4 discloses a pulse magnetic stimulation device used for therapy of urinary incontinence. This invention uses successive magnetic pulses, and thus a capacitor needs to be rapidly and repeatedly charged and discharged. The description of an electric circuit disclosed in the invention is only that: a power supply voltage is 100 to 3 kV; the capacity of the capacitor is 300 μF; and a protective resistor prevents a rush current, and, for example, problems of an increase in power consumption and heat generation of an internal element which occur with successive generation of magnetic pulses are not particularly described.

CITATION LIST

Patent Literature

[PTL 1] Japanese Laid-Open Patent Publication No. 2010-200446
[PTL 2] Japanese Laid-Open Patent Publication No. 2003-9548
[PTL 3] Japanese Laid-Open Patent Publication No. 2004-255104
[PTL 4] Japanese Laid-Open Patent Publication No. 9-276418

SUMMARY OF THE INVENTION

Problems to be Solved by the Invention

A pulse current is generated by momentarily discharging electric charge stored in a capacitor. This process is common to industrial equipment, medical equipment, and medical magnetic stimulation devices. Among the above devices, a device that generates a pulse having a low voltage or a small width has low energy, thus the capacitor has a low capacity, and a charging time of the capacitor is short. Meanwhile, a device that needs to successively generate magnetic stimulation pulses having high energy as in a medical magnetic stimulation device needs to repeatedly charge and discharge a high-capacity capacitor at a high speed. In general, a discharging time is much shorter than a charging time. For this reason, the charging time of the capacitor has to be shorter than or substantially equal to the discharging time interval of successive pulses.

In order to shorten the charging time, it is necessary to considerably increase a charge current. For this purpose, it is necessary to (1) increase the voltage and the capacity of a step-up transformer which generates a high voltage, (2) increase the capacity of a bridge circuit section which rectifies a voltage from the step-up transformer, (3) increase the capacity of a limiting resistor which limits the charge current, and (4) adopt a multi-channel system including a plurality of capacitors and a charging circuit, according to circumstances. They all mean a considerable increase in device size, weight, and power consumption. Thus, a magnetic pulse generation device capable of generating successive pulses is heavy and has great power consumption, and a small-sized and lightweight successive magnetic pulse generation device has not been realized.

Due to these reasons, it is difficult to carry and move a medical successive pulse magnetic stimulation device which is increased in size and weight. In addition, commercial power 100 V is insufficient for the device, and thus a place where the device can be used is limited. If successive pulse magnetic stimulation by a portable power supply operating with commercial power 100 V is enabled, control of muscle contraction with magnetic pulses is easily performed in a hospital room without using a skin electrode. The successive magnetic pulse stimulation does not involve pain as in electric stimulation and has an advantage that great muscle contraction can be caused in the extremities, and thus application thereof in the field of rehabilitation can be expanded.

A main object of the present invention is to reduce the size of a medical successive pulse magnetic stimulation device as is understood from the above-described contents, and reduce the sizes and the weights of components and shorten a charging time for this purpose. An additional object of the present invention is to configure a magnetism generation means as a mono-phase type to be used for special magnetic therapy, to configure the magnetism generation means as a bi-phase type to double stimulation, thereby obtaining a high therapeutic effect, and further to alleviate magnetic stimulation by using vibration.

Solution to the Problems

In view of the above-described problems, the present invention has solved the above-described problems by using the following technique. One embodiment of the invention (FIGS. 1 to 4) is a medical magnetic pulse generation device including:

a discharging circuit section K in which a magnetic therapy pulse coil 6 configured to generate an eddy current in a target part 3, a charging/discharging capacitor 4, and a switching semiconductor element 7 configured to supply a discharge current from the charging/discharging capacitor 4 to the pulse coil 6 are connected in series in a loop;

a step-up transformer 1 including a primary-side coil 1*a* connected to an AC power supply 2 and a secondary-side coil 1*b* connected to an input terminal 5*a* of a full-wave rectifying circuit 5;

a control unit 8 connected to the switching semiconductor element 7 and configured to control conduction timing of the switching semiconductor element 7; and the full-wave rectifying circuit 5 having output terminals 5*b* connected to both terminals P1 and P2 of the charging/discharging capacitor 4, respectively, wherein at least either one of an inductor 9 or resistor 10 for reducing a shunt current 11*b* or 12*b* flowing from the discharging circuit section K into the full-wave rectifying circuit 5 at time of forward or reverse discharging of the charging/discharging capacitor 4 is connected between either one of the output terminals 5*b* of the full-wave rectifying circuit 5 and either one of the terminals P1 and P2 of the charging/discharging capacitor 4 or between both terminals 5*b* of the full-wave rectifying circuit 5 and the both terminals P1 and P2 of the charging/discharging capacitor 4.

One embodiment of the invention (FIGS. 5 and 6) is a medical magnetic pulse generation device including:

a discharging circuit section K in which a magnetic therapy pulse coil 6 configured to generate an eddy current in a target part 3, a charging/discharging capacitor 4, and a switching semiconductor element 7 configured to supply a discharge current from the charging/discharging capacitor 4 to the pulse coil 6 are connected in series in a loop;

a step-up transformer 1 including a primary-side coil 1*a* connected to an AC power supply 2 and a secondary-side coil 1*b* connected to an input terminal 5*a* of a full-wave rectifying circuit 5;

a control unit 8 connected to the switching semiconductor element 7 and configured to control conduction timing of the switching semiconductor element 7; and the full-wave rectifying circuit 5 having output terminals 5*b* connected to both terminals P1 and P2 of the switching semiconductor element 7, respectively, wherein at least either one of an inductor 9 or resistor 10 for reducing a shunt current 11*b* or 12*b* flowing from the discharging circuit section K into the full-wave rectifying circuit 5 at time of forward or reverse discharging of the charging/discharging capacitor 4 is connected between either one of the output terminals 5*b* of the full-wave rectifying circuit 5 and either one of the terminals P1 and P2 of the switching semiconductor element 7 or between both terminals 5*b* of the full-wave rectifying circuit 5 and the both terminals P1 and P2 of the switching semiconductor element 7.

According to embodiments of the invention, by the inductor 9 or the resistor 10, the shunt current 11*b* or 12*b* split and flowing from the discharging circuit section K into the full-wave rectifying circuit 5 at the time of forward or reverse discharging of the charging/discharging capacitor 4 can be reduced to be a very small current, so that the capacities of the bridge diodes D1 to D4 forming the full-wave rectifying circuit 5 can be small, and it is possible to reduce the size of the device.

Another embodiment is directed to a medical successive magnetic pulse generation device, wherein a relationship between: a total inductance L which is a total sum of inductance of a charging circuit section J1 including the secondary-side coil 1*b* of the step-up transformer 1 and at least either the inductor 9 for reducing the shunt current 11*a* or 12*b* or the resistor 10 for reducing the shunt current 11*a* or 12*b* in the medical successive magnetic pulse generation device or a total sum of inductance of a charging circuit section J2 including the secondary-side coil 1*b* of the step-up transformer 1, at least either the inductor 9 for reducing the shunt current 11*a* or 12*b* or the resistor 10 for reducing the shunt current 11*a* or 12*b*, and the pulse coil 6 in the medical successive magnetic pulse generation device; a total DC resistance R which is a total sum of DC resistance of the charging circuit section J1 or J2; and a capacitance C of the charging/discharging capacitor 4, satisfies the following formula "Math. 1" thereby to configure a resonance type charging circuit, and the relationship between the total inductance L, the capacitance C, and the total DC resistance R satisfies the following formula "Math. 2". If the following two formulas are satisfied, the inductor 9 and the resistor 10 for the very small shunt currents 11*b* and 12*b* may not be provided.

$$R < 2\sqrt{L/C} \quad \text{[Math. 1]}$$

$$0.5T < \frac{2\pi}{\sqrt{\frac{1}{LC} - \left(\frac{R}{2L}\right)^2}} < 2T \quad \text{[Math. 2]}$$

Since mathematical formula 1 is satisfied, it is possible to complete charging of the charging/discharging capacitor 4 only by generating a charge pulse P in a short time. Since mathematical formula 2 is satisfied, an inflow time (=a charging time t) of the charge current to the charging/discharging capacitor 4 can be made similar to a successive pulse repeating time interval T (0.5 T to 2 T). In addition, as is understood from Example 1 described later, it is possible to nearly complete the charging before the next discharging timing of the charging/discharging capacitor 4, while the magnitude of the charge current is sufficiently reduced. In other words, the charging time t is preferably equal to or less than the successive pulse repeating time interval T. That is, if the charging time t is 0.5 T to 1 T, sufficient charging is possible, and if the charging time t exceeds 1 T and not greater than 2 T, charging of the charging/discharging capacitor 4 does not reach full charging but reaches a level at which the charging/discharging capacitor 4 can be used for therapy. If the charging time t exceeds 2 T, charging becomes insufficient, causing insufficient magnetic stimulation. By shortening the charging time t as described above, successive generation of strong magnetic pulses can be enabled.

Another embodiment relates to the switching semiconductor element 7, and the switching semiconductor element 7 is a thyristor 7a alone or includes the thyristor 7a and an inversion current diode 7b or bidirectional conductive element 7c connected in reverse parallel to the thyristor 7a.

According to an embodiment, in the case where the switching semiconductor element 7 is the thyristor 7a alone connected to the charged capacitor 4 in a forward direction, the discharge current 11 in the forward direction flowing through the pulse coil 6 becomes a mono-phase current, and can be used for a strong plastic revulsion method. Meanwhile, in the case where the switching semiconductor element 7 includes the thyristor 7a connected to the charged capacitor 4 in the forward direction and the inversion current diode 7b or the bidirectional conductive element 7c connected in reverse parallel to the thyristor 7a, the discharge current flowing through the pulse coil 6 becomes a bi-phase current composed of the discharge current 11 in the forward direction and an inversion current 12 in a reverse direction following the discharge current 11. With a single discharge, peripheral nerves can be stimulated twice, the therapeutic effect can be enhanced, and charging with the shunt current 11a or 12a returning to the capacitor 4, of the discharge current 11 or the inversion current 12, is enabled, so that the amount of the next charge can be reduced. The shunt currents 11a and 12a are nearly equal to the discharge current 11 and the inversion current 12 as described later.

One embodiment is directed to the a medical magnetic pulse generation device, wherein a vibration member 6a is further disposed on a surface of the pulse coil 6 at a target part 3 side or a surface of the pulse coil 6 at a side opposite to the target part 3 side.

When the vibration member 6a is disposed on the surface of the pulse coil 6 at the target part 3 side (that is, an affected part side) or the surface of the pulse coil 6 at the side opposite to the target part 3 side, the vibration member 6a vibrates due to magnetism generated intermittently at the pulse coil 6, to provide mechanical vibration to the target part 3 side (that is, the affected part side), whereby stimulation of peripheral nerves by the eddy current generated intermittently can be relieved, and an uncomfortable feeling during magnetic therapy can be alleviated. As the vibration member 6a, a ferromagnetic material magnetized strongly by a magnetic field, for example, a block or a plate of iron, cobalt, nickel, an alloy thereof, ferrite, or the like is used.

Advantageous Effects of the Invention

According to the present invention, the problem of an increase in charge current which is a major obstacle to successive generation of strong magnetic pulses for peripheral nerve stimulation from the medical magnetic pulse generation device can be solved without using a high-capacity resistor having large power consumption, a heavy, bulky, and large-sized step-up transformer, a charging circuit configured as a multi-channel type, etc., and it is possible to achieve size and weight reduction and power saving of the device. Due to the size reduction and power saving, the chance of using a medical successive magnetic pulse generation device which it is conventionally difficult to transport so that a place where the device is used is limited can be expected to be further increased. In addition, by devising the circuit, special therapy can be performed by changing a condition for generating a magnetic field, the therapeutic effect by strong stimulation can be improved, and therapy performed by a conventional electric stimulation device can be replaced with therapy performed with magnetic stimulation that causes less pain and is easily handled.

DESCRIPTION OF EMBODIMENTS

Figure 1:
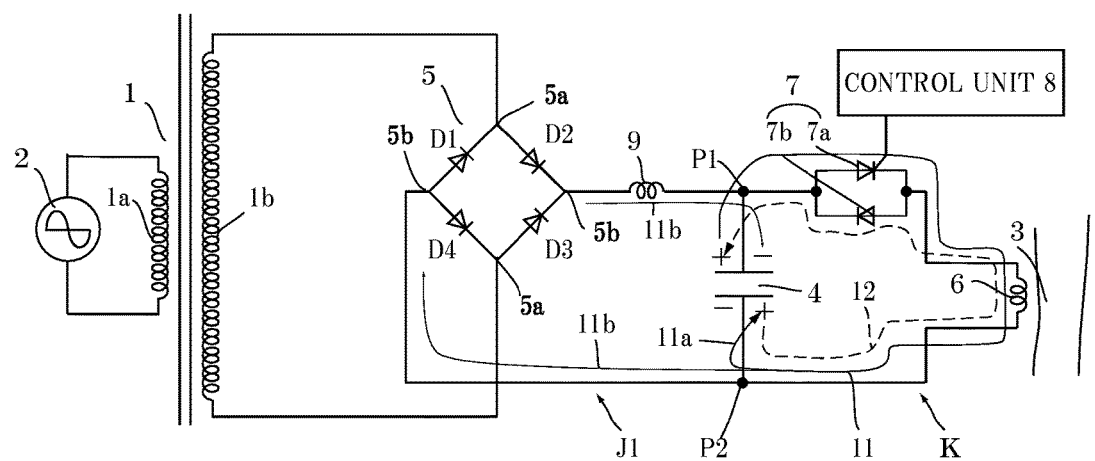
FIG. 1 shows a first embodiment of a circuit of a medical successive magnetic pulse generation device according to the present invention.

Hereinafter, the present invention will be described in accordance with illustrated embodiments. A main object of the present invention is to reduce the size of a medical successive magnetic pulse device, and in addition to this, the present inventors have conducted thorough research with the aim of solving problems of: handling of a shunt current passing through a full-wave rectifying circuit; and an increase in a charge current to a charging/discharging capacitor 4 which is the biggest problem that hinders size reduction. As a result, the present inventors have found the following. Firstly, by reducing a shunt current 11b or 12b flowing into a full-wave rectifying circuit 5 at the time of discharging of the charging/discharging capacitor 4, the capacities of bridge diodes D1 to D4 which form the full-wave rectifying circuit 5 can be considerably reduced. In other words, the shunt current 11b or 12b flowing at the time of discharging of the charging/discharging capacitor 4 in a forward direction (FIG. 1) or at the time of voltage inversion (FIG. 5) and passing through the full-wave rectifying circuit 5 can be reduced with low resistance and/or low inductance; secondly, by appropriately setting a mutual relationship between the aforementioned total inductance L and total DC resistance R in the circuit within the device and a capacitance C of the charging/discharging capacitor 4, a charge current in the forward direction is sufficiently reduced, and a charging speed at which generation of successive magnetic pulses is possible is obtained; and thirdly, when magnetic pulses generated at a pulse coil 6 are caused to have a bi-phase (plus-minus bimodal type) waveform in the forward direction and a reverse direction by configuring a switching semiconductor element 7 that is a discharging element connected in parallel to the charging/discharging capacitor 4, as a bidirectional type to enable reverse discharge from the charging/discharging capacitor 4 by a diode 7b (or a bidirectional conductive element 7c) of the switching semiconductor element 7, electric stimulation can be applied twice by a single charge, thereby doubling a therapeutic effect, and power consumption can be reduced by recharging the charging/discharging capacitor 4 at the same time, or the way to special magnetic stimulation therapy is paved by making the magnetic pulses to have a mono-phase waveform with which electric stimulation is performed once by a single charge. The following means and conditions based on these findings allow a medical successive pulse magnetic stimulation device to be reduced in size and weight.

As described above, when a conventional medical successive magnetic pulse generation device is applied as it is, the device has to be large in size and heavy. When an explanation is given again, the cause for this is that if the interval between magnetic pulses applied to an affected part is shortened, a time sufficient to charge a charging/discharging capacitor cannot be ensured, and thus the charge current has to be increased. The magnitude of the charge current is controlled generally by inserting, between a step-up transformer and the charging/discharging capacitor, a resistor which limits a current. The resistor generates heat by a current, and thus there is inevitably great power loss in the current limiting resistor. For example, in the case of charging a capacitor of 100 μF with DC 1000 V, if a resistor of 1 kΩ is used to prevent a rush current, a current of 1 A flows, so that the capacitor can be charged in 1 second. However, the resistor involves generation of a great Joule heat of 1 kW. Thus, if the resistance value is increased to 10 kΩ, the current decreases to 0.1 A, and the heat generated reduces to 100 W, but the charging time increases to 10 seconds. That is, in order to use the resistor as a current limiting element to generate successive magnetic pulses, it is necessary to (1) decrease the resistance value of the current limiting resistor and increase the heat capacity of the current limiting resistor, or (2) configure a charging circuit as a multi-channel type and cause magnetic pulses to be generated sequentially, and each of these measures becomes a cause for size increase of the device.

Therefore, in the present invention, the total inductance of the present circuit (the total inductance including a secondary-side coil 1b of a step-up transformer 1 and an inductor 9 for reducing the shunt current 11b or 12b passing through the full-wave rectifying circuit 5, and in addition to them, the pulse coil 6 is included depending on a circuit) is used as an element that limits a current. That is, research has been conducted as to a circuit employing a method for reducing a sudden increase in current at the time of start of charge to control a charge current, by the high total inductance of the present circuit. An example of a circuit diagram of a successive magnetic pulse generation device using the present invention is shown in FIG. 1.

The circuit in FIG. 1 includes a discharging circuit section K and a charging circuit section J1. The discharging circuit section K is used by being made close to or brought into contact with a target part 3 of a patient, and is configured by connecting, in series in a loop, the magnetic therapy pulse coil 6 which generates an eddy current in the form of successive pulses having a very short time in muscles to stimulate peripheral nerves at the muscles, the charging/discharging capacitor 4, and the switching semiconductor element 7 which supplies a discharge current 11 from the charging/discharging capacitor 4 to the pulse coil 6. In this embodiment, the switching semiconductor element 7 includes: a thyristor 7a directed in a forward direction from one output terminal 5b of the full-wave rectifying circuit 5 from which output terminal 5b a charge current is outputted, toward the pulse coil 6; and the inversion current diode 7b which is connected in reverse parallel to the thyristor 7a. In FIG. 1, the inductor 9 for reducing the shunt current is connected in series between the one output terminal 5b and a terminal P1 of the switching semiconductor element 7. A control unit 8 controls conduction timing of the switching semiconductor element 7 (=successive magnetic pulse repeating time interval T) and is connected to the thyristor 7a of the switching semiconductor element 7.

The charging circuit section J1 includes the secondary-side coil 1b of the step-up transformer 1, the full-wave rectifying circuit 5, the inductor 9 for reducing the shunt current (or a resistor 10, for reducing the shunt current, which is used instead of the inductor 9), and the charging/ discharging capacitor 4. The step-up transformer 1 includes a primary-side coil 1a connected to an AC power supply 2 and the secondary-side coil 1b connected to input terminals 5a of the full-wave rectifying circuit 5. Both output terminals 5b of the full-wave rectifying circuit 5 are connected to both terminals P1 and P2 of the charging/discharging capacitor 4, respectively. At least either the inductor 9 for reducing the shunt current or the resistor 10 for reducing the shunt current is connected between either one of the output terminals 5b of the full-wave rectifying circuit 5 and either one of the terminals P1 and P2 of the charging/discharging capacitor 4 or between both terminals 5b and P1 (5b, P2). That is, there is the case where only the inductor 9 for reducing the shunt current or only the resistor 10 for reducing the shunt current is connected in series either between the terminal P1 and the one output terminal 5b from which the charge current is outputted, or between the other output terminal 5b and the terminal P2, the case where the inductor 9 is provided between the one output terminal 5b and the terminal P1 and the resistor 10 is connected between the other output terminal 5b and the terminal P2 or vice versa, or the case where the inductors 9 or the resistors 10 are connected between the output terminal 5b and the terminal P and between the output terminal 5b and the terminal P2, respectively.

Figure 2:
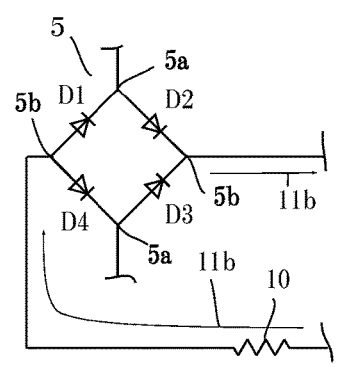
FIG. 2 is a partial diagram of a first modification of FIG. 1.

FIG. 2 shows an example where the resistor 10 is used instead of the inductor 9 for reducing the shunt current. Regarding the arrangement positions of the inductor 9 and the resistor 10, each of the inductor 9 and the resistor 10 may be connected in series to either the one output terminal 5b of the full-wave rectifying circuit 5 or the other output terminal 5b at the opposite side as described above.

Figure 5:
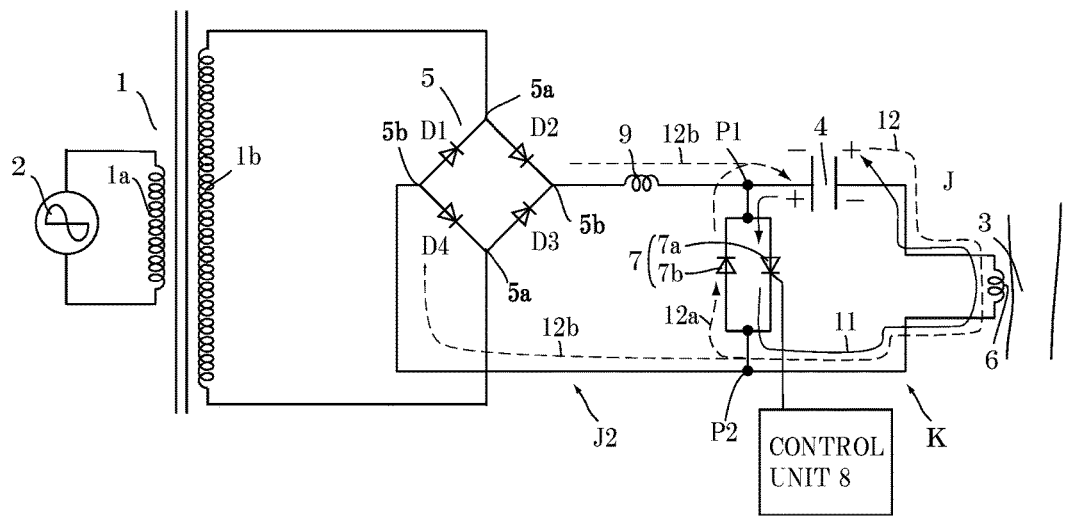
FIG. 5 shows a second embodiment of the circuit of the medical successive magnetic pulse generation device according to the present invention.

Similarly, another example of the circuit diagram of the medical successive magnetic pulse generation device using the present invention is shown in FIG. 5. In this circuit, only the positions of the charging/discharging capacitor 4 and the switching semiconductor element 7 are interchanged with each other, and the other configuration is the same as in FIG. 1. In this case, the input-side terminal P1 of the thyristor 7a is connected to the output terminal 5b side of the full-wave rectifying circuit 5 which is a side from which the charge current is outputted.

In the circuit of FIG. 1 or 5, when a commercial current flows through the primary-side coil 1a of the step-up transformer 1, a current flows through the secondary-side coil 1b in a state where the voltage is boosted to a predetermined voltage. The secondary-side current is rectified by the full-wave rectifying circuit 5, and then is stored into the charging/discharging capacitor 4 via the inductor 9 for reducing the shunt current (or the resistor 10 for reducing the shunt current, although not shown) (see FIG. 9). When a trigger signal is provided from the control unit 8 to the thyristor 7a to cause the electric charge stored in the charging/discharging capacitor 4 (the discharge current 11 in the forward direction) to flow through the pulse coil 6 in the forward direction momentarily, a strong pulse magnetic field in the forward direction occurs at the pulse coil 6 to generate an eddy current in muscles at an affected part located in contact with or closely to the pulse coil 6, thereby stimulating peripheral nerves. At the time of the discharge in the forward direction, in the case of FIG. 1, the discharge current 11 having passed through the pulse coil 6 is split to flow through the inversion current (backflow) diode 7b and the full-wave rectifying circuit 5 and returns to the charging/discharging capacitor 4 again. The shunt current 11b which flows through the full-wave rectifying circuit 5 and returns to the charging/discharging capacitor 4 again is considerably reduced due to the presence of the inductance 9 (or the resistor 10), becomes much lower than a shunt current 11a which directly returns to the charging/discharging capacitor 4, thus does not damage the diodes D1 to D4 of the full-wave rectifying circuit 5, and almost does not inhibit charging of the charging/discharging capacitor 4 with the shunt current 11a in the reverse direction. As a result, the charging/discharging capacitor 4 enters a state where a voltage is stored in the reverse direction by the shunt current 11a. Subsequently, an inversion current in the reverse direction is discharged from the charging/discharging capacitor 4 charged with the voltage in the reverse direction, and a magnetic field in the reverse direction is formed at the pulse coil 6 to generate an eddy current in the muscles at the affected part similarly as described above, thereby stimulating the peripheral nerves.

In the case of FIG. 5, at the time of the above-described discharge in the forward direction, the discharge current 11 having passed through the pulse coil 6 directly returns to the charging/discharging capacitor 4, and the charging/discharging capacitor 4 enters a state where a voltage is stored in the reverse direction. Then, an inversion current 12 in the reverse direction is discharged from the charging/discharging capacitor 4 charged with the voltage in the reverse direction, a magnetic field in the reverse direction is formed at the pulse coil 6 to generate an eddy current in the muscles at the affected part similarly as described above, thereby stimulating the peripheral nerves. The inversion current 12 is split at the terminal P2, so that a shunt current 12a and a shunt current 12b flow through the inversion current diode 7b and through the full-wave rectifying circuit 5, respectively, and are stored into the charging/discharging capacitor 4 again. The shunt current 12b which flows through the full-wave rectifying circuit 5 and returns to the charging/discharging capacitor 4 again is considerably reduced due to the presence of the inductance 9 (or the resistor 10), becomes much lower than the shunt current 11a which flows through the backflow diode 7b and directly returns to the charging/discharging capacitor 4, and thus does not damage the diodes D1 to D4 of the full-wave rectifying circuit 5. That is, in the circuit in FIG. 1 or 5, a magnetic field waveform (the magnetic field is a plus-minus bimodal type pulsed magnetic field in which the waveform projects once in each of both pole directions) that is a so-called bi-phase waveform is created and the discharge is ended.

Figure 9:
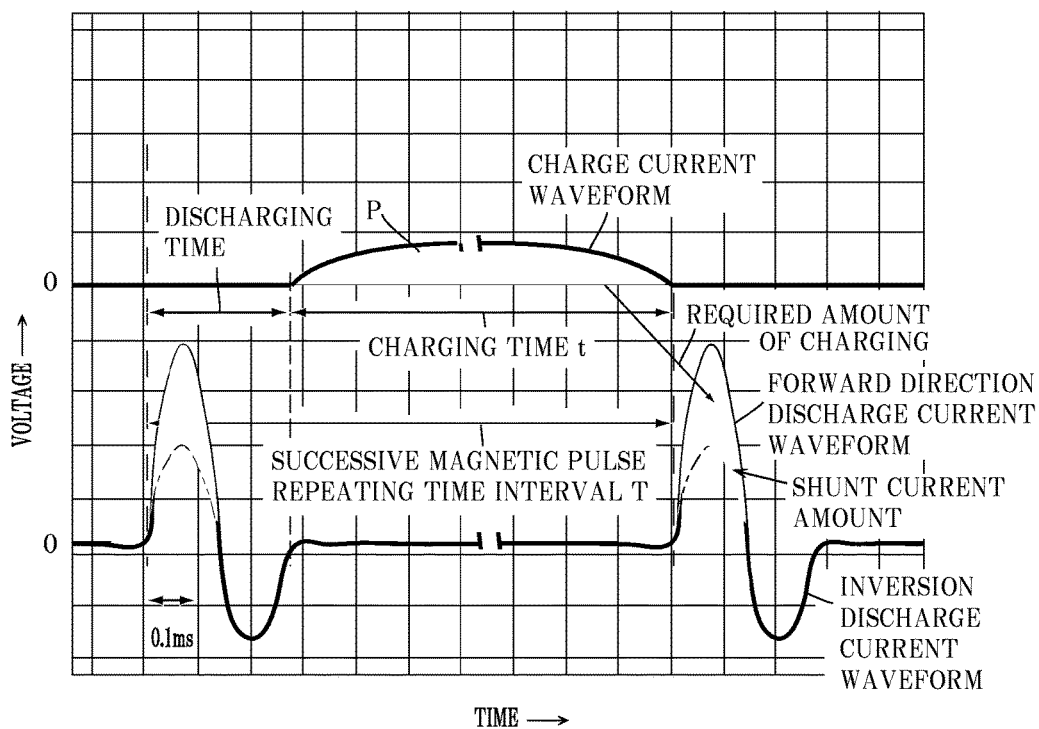
FIG. 9 is a diagram of a charge waveform and a discharge waveform at the time of bi-phase discharge according to the present invention.

Due to this recharging, the charging/discharging capacitor 4 gets back electric charge equivalent to considerable part of the electric charge stored in the charging/discharging capacitor 4 before the discharge, and the energy provided from the charging circuit section J1 or J2 into the charging/discharging capacitor 4 becomes only the hatched portion and is considerably reduced (FIG. 9). Therefore, it is possible to reduce the sizes of the elements used in the device, as compared to a device employing a mono-phase method described later, and considerable reduction in the size and the weight of the device and considerable energy saving of the device are expected.

Figure 3:
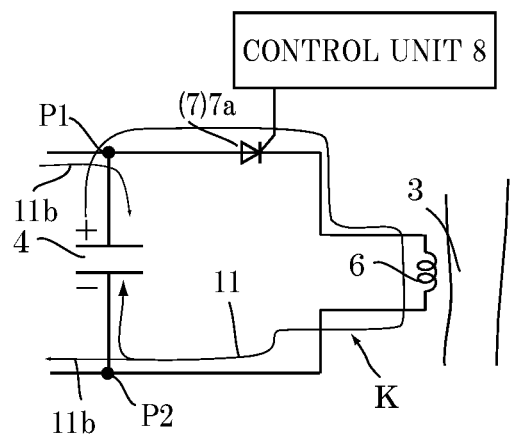
FIG. 3 is a partial diagram of a second modification of FIG. 1.

FIG. 3 shows the case where the switching semiconductor element 7 in FIG. 1 is composed of the thyristor 7a alone. In this case, since the backflow diode 7b is not present, the inversion current 12 does not flow through the pulse coil 6, the magnetic field that occurs at the pulse coil 6 becomes a magnetic field in the form of pulses projecting only in a single pole direction (see FIG. 8), so that a magnetic field waveform that is a so-called mono-phase waveform is created and the discharge is ended. In this case, the voltage in the charging/discharging capacitor 4 is 0 or negative, and the charging/discharging capacitor 4 is charged from this state. Thus, charging of the charging/discharging capacitor 4 from the charging circuit section J1 requires great electric power as compared to the case of the bi-phase method. This is shown by hatching in FIG. 8. Also in this case, the shunt current 11b of the discharge current 11 in the forward direction flows through the full-wave rectifying circuit 5, but is reduced by the inductor 9 (or the resistor 10), so that the bridge diodes D1 to D4 of the full-wave rectifying circuit 5 are protected similarly as described above.

Figure 4:
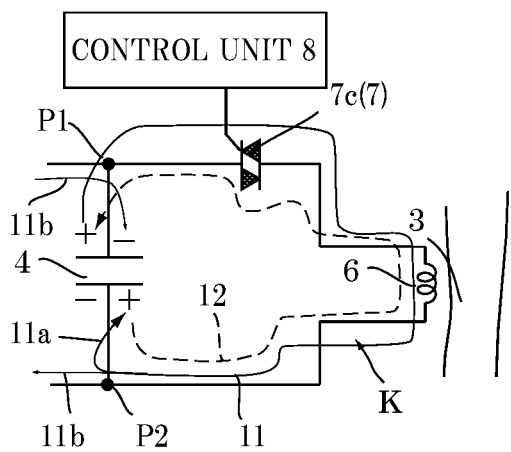
FIG. 4 is a partial diagram of a third modification of FIG. 1.
Figure 6:
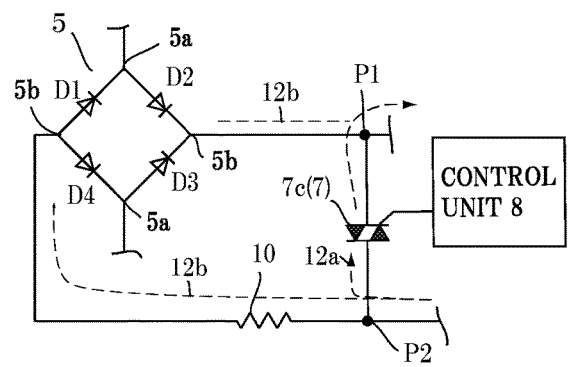
FIG. 6 is a partial diagram of a further modification of FIG. 5.
Figure 7:
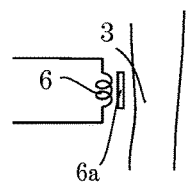
FIG. 7 is a partial diagram in which a vibration member is provided to a pulse coil in the circuit in FIGS. 1 to 6.

FIGS. 4 and 6 each show the case where the switching semiconductor element 7 in FIG. 1 or 5 is the bidirectional conductive element (triac) 7c, a trigger signal is received from the control unit 8 in both directions, the discharge current 11 in the forward direction and the inversion current 12 in the reverse direction are caused to flow, and magnetic stimulation is performed by the bi-phase method. The other is the same as in FIGS. 1 and 5.

Figure 8:
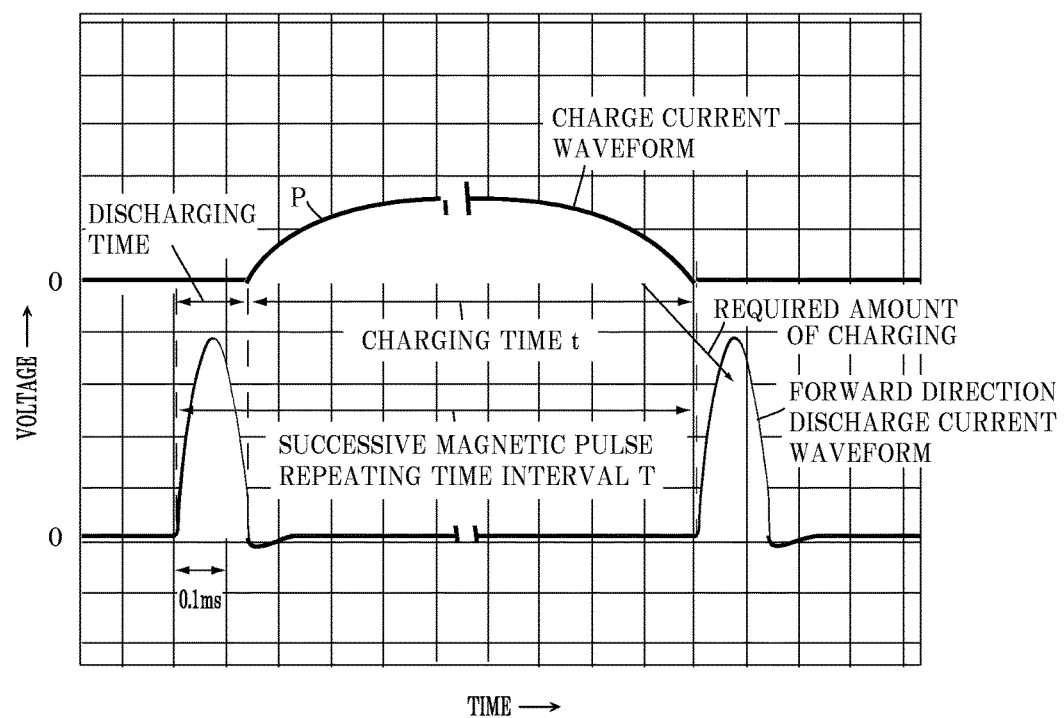
FIG. 8 is a diagram of a charge waveform and a discharge waveform at the time of mono-phase discharge according to the present invention.

When the characteristics of the elements within the above-described circuit are set in accordance with "mathematical formula 1", it is possible to complete charging of the charging/discharging capacitor 4 only by generating a charge pulse P shown by the charge current waveform in FIG. 8 or 9 in a short time.

That is, in the charging circuit section J1 in FIG. 1, a relationship between: a total inductance L which is a total sum of inductance including the inductance of the secondary-side coil 1b of the step-up transformer 1, and the inductance of the inductor 9 in the case where the inductor 9 is used instead of the resistor 10 or together with the resistor 10; a total DC resistance which is a total sum of DC resistance including the DC resistance of the secondary-side coil 1b of the step-up transformer 1, and the DC resistance of the inductor 9 in the case where the inductor 9 is used as described above and the DC resistance of the resistor 10 in the case where the resistor 10 is used instead of the inductor 9 or together with the inductor 9; and the capacitance C of the charging/discharging capacitor 4, satisfies "mathematical formula 1", whereby the present circuit is configured as a resonance type charging circuit.

That is, the total inductance L of the charging circuit section J1 may be (i) only the inductance of the secondary-side coil 1b or may be (ii) the inductance of the secondary-side coil 1b+the inductance of the inductor 9, and the total DC resistance R of the charging circuit section J1 may be (a) only the DC resistance of the secondary-side coil 1b, may be (b) the DC resistance of the secondary-side coil 1b+the DC resistance of the inductor 9, may be (c) the DC resistance of the secondary-side coil 1b+the resistor 10, or may be (d) the DC resistance of the secondary-side coil 1b+the DC resistance of the inductor 9+the resistor 10.

In the charging circuit section J2 in FIG. 5, the pulse coil 6 is further added to the case of FIG. 1, and a relationship between: a total inductance L which is a total sum of inductance including the inductance of the secondary-side coil 1b of the step-up transformer 1, the inductance of the pulse coil 6, and the inductance of the inductor 9 in the case where the inductor 9 is used instead of the resistor 10 or together with the resistor 10; and a total DC resistance R which is a total sum of DC resistance including the DC resistance of the secondary-side coil 1b of the step-up transformer 1, the DC resistance of the pulse coil 6, and the DC resistance of the inductor 9 in the case where the inductor 9 is used as described above and the DC resistance of the resistor 10 in the case where the resistor 10 is used instead of the inductor 9 or together with the inductor 9, satisfies "mathematical formula 1", whereby the present circuit is configured as a resonance type charging circuit. Accordingly, charging is performed with a charge current waveform in the form of short-width pulses as shown in FIGS. 8 and 9, not with an attenuation type current waveform in which a current gradually attenuates as in a conventional device, so that charging of the charging/discharging capacitor 4 can be completed in a short time as described above.

$$R < 2\sqrt{L/C}$$ [Math. 1]

By satisfying "mathematical formula 2", a charge current inflow time t when the charge current flows into the charging/discharging capacitor 4 can be made similar to the successive pulse repeating time interval T. In other words, by causing the charge current inflow time t to exceed half the successive pulse repeating time interval T but be less than two times of the successive pulse repeating time interval T, repetition of the successive pulses can be achieved. In this range, the charge current inflow time t preferably exceeds 0.5 T and is equal to or less than 1 T. If the charge current inflow time t is made shorter than 0.5 T, the amount of the charge current becomes excessively large, which deviates from the purpose of reducing the size of the device. If the charge current inflow time t is equal to or longer than 2 T, excessive time is taken for charging, and the charge voltage becomes insufficient.

$$0.5T < \frac{2\pi}{\sqrt{\frac{1}{LC} - \left(\frac{R}{2L}\right)^2}} < 2T$$ [Math. 2]

The above point will be described in detail. The integrated value of the charge pulse P (=the hatched portion of the charge current waveform in FIG. 8 or 9) corresponds to the amount of charging electric charge in the charging/discharging capacitor 4 (=the hatched portion of a discharge current waveform in FIG. 8 or 9). In order to minimize a load on the elements within the circuit, similar integrated values are desirably obtained by lowering the height of the charge pulse P and increasing the width of the charge pulse P. However, if this width excessively increases, charging with the charge pulse P has not been completed before the next discharge. Thus, it is necessary to make the width of the charge pulse P, that is, the inflow time t of the charge current to the charging/discharging capacitor 4, similar to the successive pulse repeating time interval T. The width of the charge pulse P (the charging time t) can be represented by a mathematical formula that is the middle part of "mathematical formula 2". If this value is set in a range of 0.5 times to 2.0 times of the successive pulse repeating time interval T, charging can be nearly completed before the next discharging timing of the charging/discharging capacitor 4, while the charge current is sufficiently reduced as described above. In addition, in the case of a device that is used while the pulse coil 6 is replaced with various ones depending on the intended use of the device, a result obtained by calculation using the value of the inductance of each coil desirably satisfies "mathematical formula 2".

The inductor 9 and the resistor 10 described above are elements that are intended for adjustment to configure the charging circuit sections J1 and J2 which satisfy "mathematical formula 1" and "mathematical formula 2" and that are small elements for supplementing insufficient inductance and resistance. If the inductor 9 or the resistor 10 replaces a large-capacity resistor in the conventional device, considerable reduction in size and weight of the device is possible. In addition, if "mathematical formula 1" and "mathematical formula 2" are satisfied even without these elements, the elements themselves are unnecessary and can be omitted. However, at least either one of the elements is required as an element for reducing the shunt current 11b or 12b as described later again.

Figure 15:
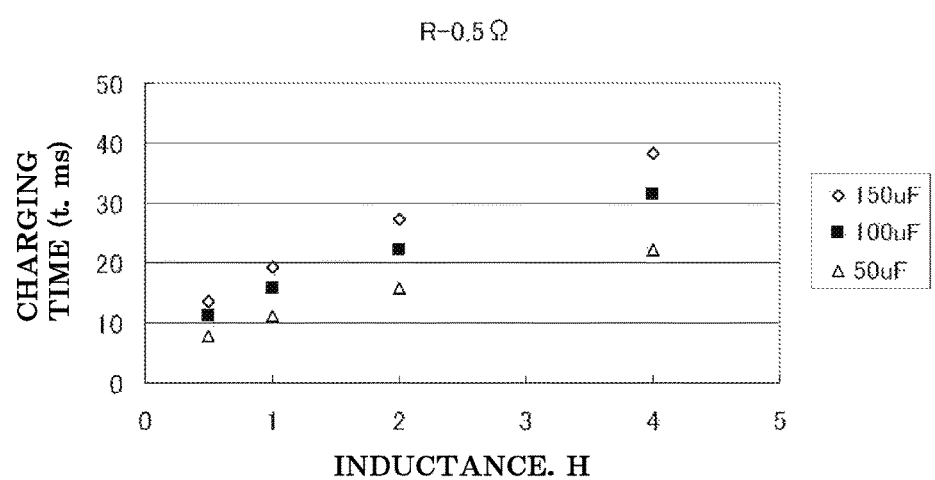
FIG. 15 is a diagram showing a relationship between: a reactance and a capacitor; and a time when a current flowing into a capacitor of an LCR resonance type circuit becomes the maximum, in the present invention.

FIG. 15 shows the results obtained by calculating the inflow time t of the charge current to the charging/discharging capacitor 4 on the basis of "mathematical formula 2" in the case where the total DC resistance R of the present circuit is made constant at 0.5Ω, the capacitance of the charging discharging capacitor 4 is set at 50, 100, and 150 microfarads (μF), and the total inductance L is changed in a range of 0.5 to 4 henrys (H). The results in FIG. 15 are almost the same even when the resistance R is changed in a range of 0.1 to 1Ω. The characteristics of the element can be roughly determined by using FIG. 15. For example, to set the charging time t of the charging/discharging capacitor 4 when the successive magnetic pulse interval T is set at 20 to 40 milliseconds, it is understood that if the capacitance of the charging/discharging capacitor 4 is 100 to 150 μF, it is necessary to design the present circuit such that the inductance of the present circuit becomes 2 to 4 H.

Figure 10:
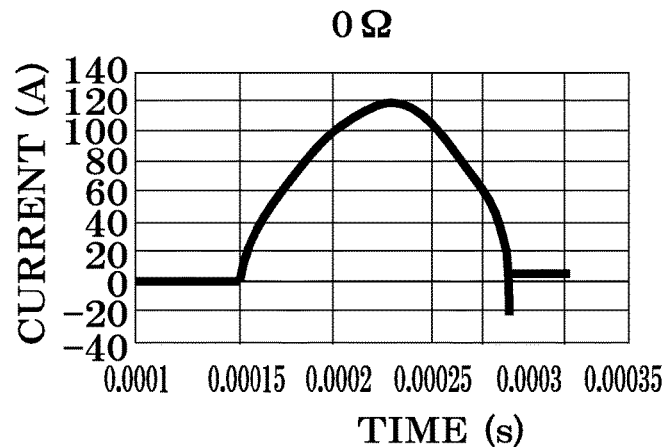
FIG. 10 shows a waveform of a current flowing through a full-wave rectifying circuit in the case where the resistance value of a resistor for a shunt current passing through the full-wave rectifying circuit in the present invention is zero.
Figure 11:
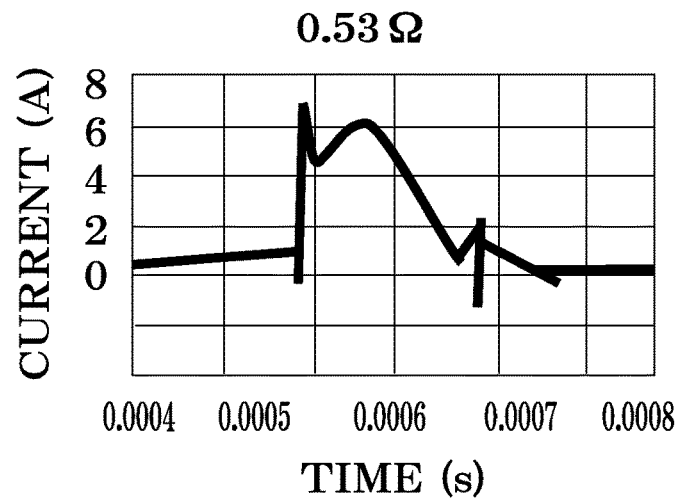
FIG. 11 shows a waveform of a current flowing through the full-wave rectifying circuit in the case where the resistance value of the resistor for the shunt current passing through the full-wave rectifying circuit in the present invention is 0.53Ω.
Figure 12:
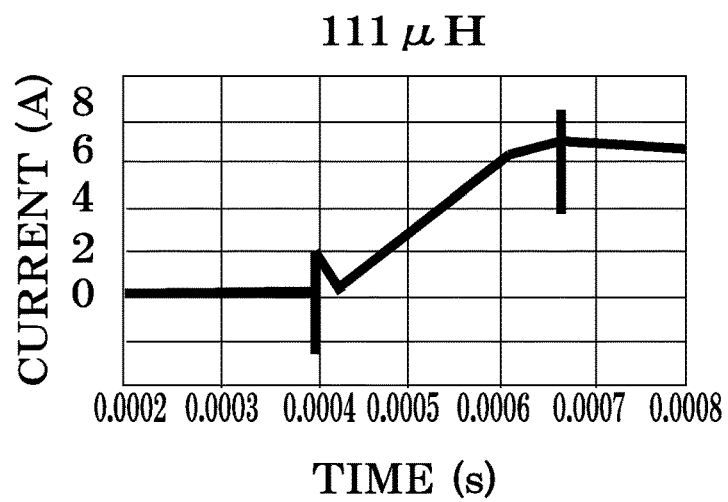
FIG. 12 shows a waveform of a current flowing through the full-wave rectifying circuit in the case where the inductance value of an inductor for the shunt current passing through the full-wave rectifying circuit in the present invention is 111 μH.

If the circuit employing the method according to the present invention is used, the shunt current 11b (FIG. 1) of the discharge current 11 in the forward direction of the charging/discharging capacitor 4 as described above or the shunt current 12b at the time of voltage inversion flows through the full-wave rectifying circuit (bridge rectifier) 5. The direction of the current flowing through this power supply circuit is shown by curved lines in FIGS. 1 and 5. Reference numeral 11 denotes flow (a narrow solid line) of the current in the forward direction at the time of discharging of the capacitor 4 that has been positively charged, and reference numeral 12 denotes flow (a narrow broken line) of the inversion current flowing at the time of capacitor voltage inversion. As described above, in the case of FIG. 1, the shunt current 11b of the discharge current 11 in the forward direction flows through the full-wave rectifying circuit 5. In the case of FIG. 5, the discharge current 11 in the forward direction does not flow through the full-wave rectifying circuit 5, but the shunt current 12b of the inversion current 12 in the reverse direction flows through the full-wave rectifying circuit 5. FIGS. 10 to 12 show the results obtained by measuring the shunt currents 11b and 12b flowing into the full-wave rectifying circuit 5. FIG. 10 shows the case where the inductor 9 and the resistor 10 are not provided, and a high current of about 120 A flows for 0.15 milliseconds (the width of the magnetic pulse). This occurs as a result of a state where any amount of current can flow since an element that impedes the shunt current 11b or 12b is not present between the full-wave rectifying circuit 5 and the charging/discharging capacitor 4. By this high current, the full-wave rectifying circuit 5 is burnt in a short time.

Meanwhile, FIG. 11 shows the case where a resistor of 0.53) is inserted as the resistor 10, the shunt currents 11b and 12b flowing into the full-wave rectifying circuit 5 reduce to about 6 A. In addition, FIG. 12 shows the case where an inductor 9 of 111 μH is inserted as the inductor 9 in FIG. 1 or FIG. 5, and the shunt currents 11b and 12b flowing into the full-wave rectifying circuit 5 reduce to about 7 A. Only by inserting the relatively small element between the full-wave rectifying circuit 5 and the charging/discharging capacitor 4 as described above, it is possible to considerably reduce the shunt currents 11b and 12b.

Next, the present invention will be described in detail on the basis of an example. This example was made for easy understanding by a person skilled in the art. That is, it should be understood that the present invention is limited by the technical idea recited in the entire specification and should not be limited only by the present embodiment.

Example 1

A successive magnetic pulse magnetic stimulation device in which the total inductance L of the charging circuit section J1 or J2 is 4.3 H, the total DC resistance is 0.5Ω, the capacitance of the charging/discharging capacitor 4 is 100 μF, and the inductance of the pulse coil 6 is 15 μH was produced on the basis of the calculation results in FIG. 15 according to the present invention. The circuit configuration was set as the configuration in FIG. 2 or FIG. 5. The output voltage of the full-wave rectifying circuit 5 was changed in a range of 350 to 600 V, the cycle of the trigger signal to the discharging element 7 was changed between 20 to 100 milliseconds, and successive magnetic pulses were generated. According to "mathematical formula 2", the time when the charge current flows into the capacitor 4 of the discharging circuit section K is 33 milliseconds (30 Hz). According to an experiment, in the case of successive magnetic pulses of 10 to 30 Hz, regarding each voltage, the charge voltage reached a storable maximum voltage before start of the next discharging, and in the case of successive magnetic pulses of 40 Hz or 50 Hz, charging was performed to 95 to 90% of the power supply voltage.

Figure 13:
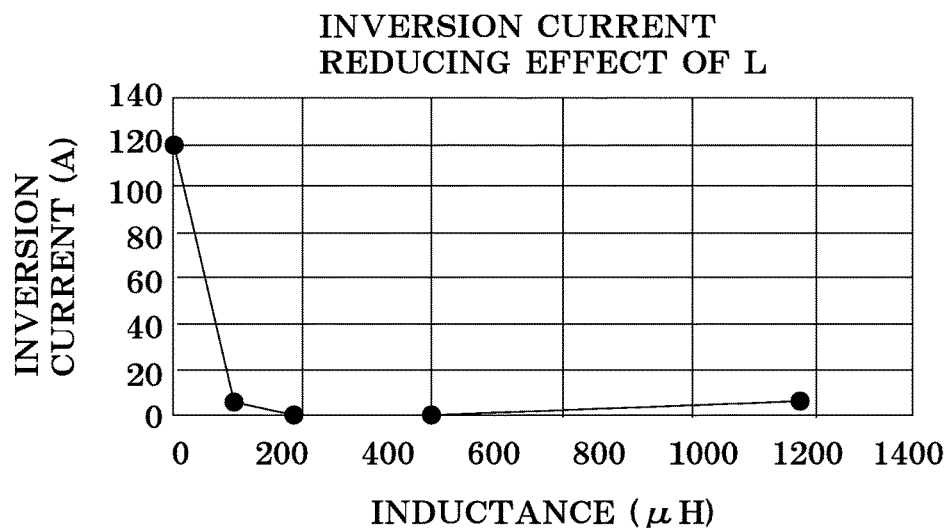
FIG. 13 is a diagram showing a reducing effect of the inductor on the shunt current passing through the full-wave rectifying circuit in the present invention.
Figure 14:
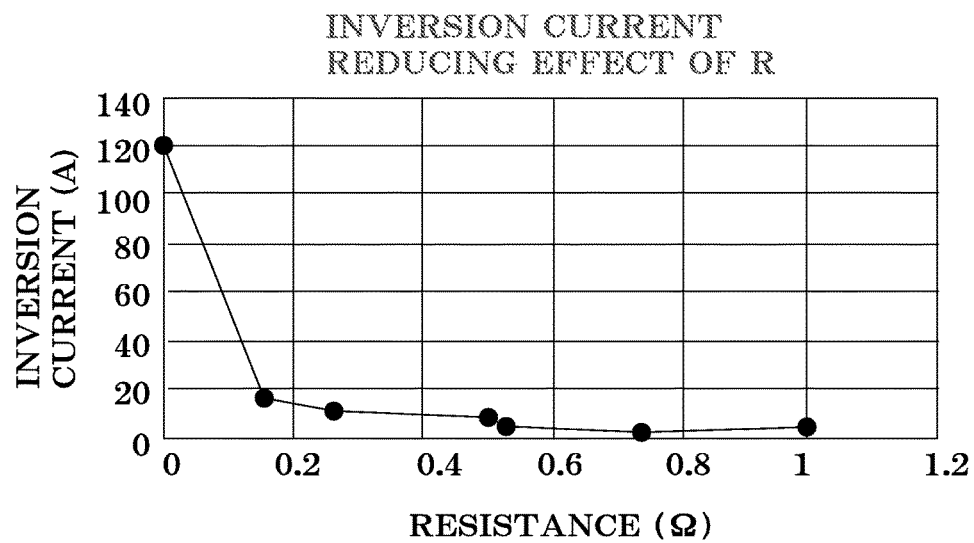
FIG. 14 is a diagram showing a reducing effect of the resistance on the shunt current passing through the full-wave rectifying circuit in the present invention.

Next, the inductance of the inductor 9 in FIG. 1 or FIG. 5 was changed between 0.11 to 1.150 mH, and the shunt current 11b or 12b flowing into the full-wave rectifying circuit 5 was measured. The results are shown in FIG. 13. In the range of tested inductances, the shunt current 11b or 12b was 7 to 3 A, and an effect of preventing breakage of the full-wave rectifying circuit 5 was obtained. However, when the inductance was increased to 1 mH or higher, the speed of charging with the successive pulses of 40 or 50 Hz further decreased. Therefore, the inductance of the inductor 9 was appropriately 0.1 to 1 mH. In addition, the resistance value of the resistor 10 in FIG. 1 or FIG. 5 was changed between 0.15 to 1.1Ω, and the shunt current 11b or 12b flowing into the full-wave rectifying circuit 5 was measured. The results are shown in FIG. 14. In the case of 0.15Ω, the shunt current 11b or 12b was 18 A and exceeded the rated current of the full-wave rectifying circuit 5, but the full-wave rectifying circuit 5 was not broken since the pulse width was short. In a range of 0.25 to 1.1Ω, the shunt current 11b or 12b was 10 to 3 A, and an effect of preventing breakage of the full-wave rectifying circuit 5 was obtained. However, when the resistance was increased to 1Ω or higher, the temperature of the resistor increased due to joule heating, so that a fan for cooling was required. From these results, the resistance value of the resistor 10 was appropriately 0.2 to 1Ω.

A conventional magnetic stimulation pulse generation device requires a very large and heavy power supply transformer or a high-voltage element, so that it is difficult to reduce the size and the weight of the conventional magnetic stimulation pulse generation device. However, by configuring magnetic stimulation with the circuit adopting the charge current reduction method described in the present application, the device can be considerably reduced in size and weight. Furthermore, as the effect of the present invention, heat generation of the power supply can be reduced, and thus it is possible to generate magnetic field pulses having such intensity as to allow for stimulation of peripheral nerves, successively for 3 hours or longer.

INDUSTRIAL APPLICABILITY

Even when movements of the extremities are hindered due to brain dysfunction, if the peripheral nerves and the muscles are normal, it is possible to largely move the extremities with less pain by stimulation with successive magnetic pulses. Furthermore, since the device using the present invention is small in size, is lightweight, and has low power consumption, the device can generate successive magnetic pulses over a long period of time. Due to these functions, the device is expected to be widely used as a device for rehabilitating a patient with tetraplegia.

DESCRIPTION OF THE REFERENCE CHARACTERS 1 step-up transformer
1a primary-side coil
1b secondary-side coil
2 AC power supply
3 target part
4 charging/discharging capacitor
P1, P2 terminal
5 full-wave rectifying circuit
5a input terminal
5b output terminal
D1 to D5 bridge diode of full-wave rectifying circuit
6 pulse coil
6a vibration member
7 switching semiconductor element
7a thyristor
7b inversion current diode
7c bidirectional conductive element
8 control unit
9 inductor for reducing shunt current
10 resistor for reducing shunt current
11 discharge current (in forward direction)
11a shunt current
11b reduced shunt current
12 inversion current
12a shunt current
12b reduced shunt current
J1, J2 charging circuit section
K discharging circuit section
P charge pulse

The invention claimed is:
1. A medical magnetic pulse generation device comprising:
  a discharging circuit section in which a magnetic therapy pulse coil configured to generate an eddy current in a target part, a charging/discharging capacitor, and a switching semiconductor element configured to supply a discharge current from the charging/discharging capacitor to the pulse coil are connected in series in a loop;
  a step-up transformer including a primary-side coil connected to an AC power supply and a secondary-side coil connected to an input terminal of a full-wave rectifying circuit;
  a control unit connected to the switching semiconductor element and configured to control conduction timing of the switching semiconductor element; and the full-wave rectifying circuit having output terminals connected to both terminals of the charging/discharging capacitor, respectively, wherein
at least either one of an inductor or resistor for reducing a shunt current flowing from the discharging circuit section into the full-wave rectifying circuit at time of forward or reverse discharging of the charging/discharging capacitor is connected between either one of the output terminals of the full-wave rectifying circuit and either one of the terminals of the charging/discharging capacitor or between both terminals of the full-wave rectifying circuit and the both terminals of the charging/discharging capacitor, wherein
a relationship between:
  a total inductance (L) which is a total sum of a first inductance of a first circuit element of a charging circuit section and a second inductance of a second circuit element of the charging circuit section, wherein the first circuit element is at least either the inductor for reducing the shunt current or the resistor for reducing the shunt current, and the second circuit element is the secondary-side coil of the step-up transformer;
  a total DC resistance (R) which is a total sum of DC resistance of the charging circuit section; and
  a capacitance (C) of the charging/discharging capacitor, satisfies "Math. 1" thereby to configure a resonance type charging circuit, and
the relationship between the total inductance (L), the capacitance (C), and the total DC resistance (R) satisfies "Math. 2", $$R < 2\sqrt{L/C} \qquad \text{[Math. 1]}$$

$$0.5T < \frac{2\pi}{\sqrt{\frac{1}{LC} - \left(\frac{R}{2L}\right)^2}} < 2T \qquad \text{[Math. 2]}$$

where T in "Math. 2" denotes a successive pulse repeating time interval.

2. The medical magnetic pulse generation device according to claim 1, wherein the switching semiconductor element is a thyristor alone or includes the thyristor and an inversion current diode or bidirectional conductive element connected in reverse parallel to the thyristor.

3. The medical magnetic pulse generation device according to claim 1, wherein a vibration member is further disposed on a surface of the pulse coil at a target part side or a surface of the pulse coil at a side opposite to the target part side.

4. A medical magnetic pulse generation device comprising:
  a discharging circuit section in which a magnetic therapy pulse coil configured to generate an eddy current in a target part, a charging/discharging capacitor, and a switching semiconductor element configured to supply a discharge current from the charging/discharging capacitor to the pulse coil are connected in series in a loop;
  a step-up transformer including a primary-side coil connected to an AC power supply and a secondary-side coil connected to an input terminal of a full-wave rectifying circuit;

a control unit connected to the switching semiconductor element and configured to control conduction timing of the switching semiconductor element; and the full-wave rectifying circuit having output terminals connected to both terminals of the switching semiconductor element, respectively, wherein at least either one of an inductor or resistor for reducing a shunt current flowing from the discharging circuit section into the full-wave rectifying circuit at time of forward or reverse discharging of the charging/discharging capacitor is connected between either one of the output terminals of the full-wave rectifying circuit and either one of the terminals of the switching semiconductor element or between both terminals of the full-wave rectifying circuit and the both terminals of the switching semiconductor element, wherein a relationship between:
  a total inductance (L) which is a total sum of a first inductance of a first circuit element of a charging circuit section, a second inductance of a second circuit element of the charging circuit section, and a third inductance of the pulse coil, wherein the first circuit element is at least either the inductor for reducing the shunt current or the resistor for reducing the shunt current, and the second circuit element is the secondary-side coil of the step-up transformer;

a total DC resistance (R) which is a total sum of DC resistance of the charging circuit section; and a capacitance (C) of the charging/discharging capacitor, satisfies "Math. 1" thereby to configure a resonance type charging circuit, and the relationship between the total inductance (L), the capacitance (C), and the total DC resistance (R) satisfies "Math. 2", $$R < 2\sqrt{L/C} \qquad \text{[Math. 1]}$$

$$0.5T < \frac{2\pi}{\sqrt{\frac{1}{LC} - \left(\frac{R}{2L}\right)^2}} < 2T \qquad \text{[Math. 2]}$$

where T in "Math. 2" denotes a successive pulse repeating time interval.

* * * * *